US011173505B2

(12) United States Patent
Roos et al.

(10) Patent No.: US 11,173,505 B2
(45) Date of Patent: *Nov. 16, 2021

(54) SYSTEM AND METHOD FOR DELIVERING SPRAYED PARTICLES BY ELECTROSPRAYING

(71) Applicant: Gilbert Technologies B.V., Naarden (NL)

(72) Inventors: Rein Andre Roos, Delft (NL); Caner Umit Yurteri, Delft (NL); Johannes Cornelis Maria Marijnissen, Delft (NL)

(73) Assignee: GILBERT TECHNOLOGIES B.V., Naarden (NL)

( * ) Notice: Subject to any disclaimer, the term of this patent is extended or adjusted under 35 U.S.C. 154(b) by 139 days.

This patent is subject to a terminal disclaimer.

(21) Appl. No.: 14/369,750

(22) PCT Filed: Dec. 24, 2012

(86) PCT No.: PCT/NL2012/050927
§ 371 (c)(1),
(2) Date: Jun. 30, 2014

(87) PCT Pub. No.: WO2013/100766
PCT Pub. Date: Jul. 4, 2013

(65) Prior Publication Data
US 2014/0367478 A1 Dec. 18, 2014

(30) Foreign Application Priority Data

Dec. 29, 2011 (NL) .................................. 2008056

(51) Int. Cl.
*B05B 5/03* (2006.01)
*B05B 5/053* (2006.01)
(Continued)

(52) U.S. Cl.
CPC ............. *B05B 5/032* (2013.01); *A61M 15/02* (2013.01); *B05B 5/0255* (2013.01); *B05B 5/0535* (2013.01); *A61M 2202/0468* (2013.01)

(58) Field of Classification Search
CPC ..... B05B 5/0255; B05B 5/032; B05B 5/0535; B05B 5/1691; A61M 15/02; A61M 2202/0468
(Continued)

(56) References Cited

U.S. PATENT DOCUMENTS 5,873,523 A 2/1999 Gomez et al.
6,079,634 A * 6/2000 Noakes ................. A61M 15/02
128/200.14
(Continued)

FOREIGN PATENT DOCUMENTS

GB 2 345 010 A 6/2000
WO 00/64590 A1 11/2000

OTHER PUBLICATIONS

International Search Report, dated Mar. 18, 2013, from corresponding PCT application.

*Primary Examiner* — Cody J Lieuwen
(74) *Attorney, Agent, or Firm* — Tatonetti IP

(57) ABSTRACT

A spraying device for producing a spray of particles in a carrier gas at ambient pressure, includes a storage volume for a liquid substance; at least one nozzle having an inlet and an outlet, the nozzle inlet fluidly communicating with the storage volume; a counter electrode; an electric supply coupled between the at least one nozzle and counter electrode for providing a first potential and create a first electric field between the nozzle outlet and the counter electrode. The device further includes at least one discharge electrode coupled to the electric supply for providing a second potential between the discharge electrode and the counter electrode, the polarity of the second potential being opposite to the polarity of the first potential. The at least one nozzle and the at least one discharge electrode are arranged adjacent and parallel to each other and facing the counter electrode from a substantially same direction.

23 Claims, 4 Drawing Sheets

(51) Int. Cl.
*A61M 15/02* (2006.01)
*B05B 5/025* (2006.01)

(58) Field of Classification Search
USPC ........ 239/3, 690–698, 704–708; 128/200.14, 128/200.16; 118/620–629, 638
See application file for complete search history.

(56) References Cited

U.S. PATENT DOCUMENTS

| | | | | |
|---|---|---|---|---|
| 6,302,331 | B1* | 10/2001 | Dvorsky | A61M 15/02 239/3 |
| 6,595,208 | B1* | 7/2003 | Coffee | B05B 5/002 128/200.14 |
| 7,883,032 | B2* | 2/2011 | Davies | A61M 11/00 239/690 |
| 2004/0079360 | A1* | 4/2004 | Coffee | A61M 15/0065 128/200.14 |
| 2004/0195403 | A1* | 10/2004 | Atterbury | A61M 15/02 239/690 |
| 2005/0236501 | A1* | 10/2005 | Zimlich, Jr. | A61M 15/0065 239/690 |
| 2011/0174304 | A1* | 7/2011 | Triplett, II | A61M 15/02 128/200.23 |

* cited by examiner

SYSTEM AND METHOD FOR DELIVERING SPRAYED PARTICLES BY ELECTROSPRAYING

FIELD

The present invention relates to a system for delivering sprayed particles by electrospraying. Also, the present invention relates to a method for delivering sprayed particles by electrospraying.

BACKGROUND

Electrospraying is a process where a liquid can be distributed into uniformly sized particles under the influence of an electrical field. From a reservoir liquid is transported into a nozzle. The nozzle is coupled to one polarity of a high voltage source and functions as an electrode. A counter electrode is typically formed by a plate or mesh at some distance from the nozzle electrode, and is coupled to the other polarity of the high voltage source. By creating a high voltage between the nozzle and the counter electrode a liquid droplet at the tip of the nozzle becomes charged and atomizes due to the electrostatic forces. The atomized and charged liquid particles in the electric field between the nozzle and the counter electrode form a flow of particles, i.e., a spray. This process is known to provide a spray of uniformly sized particles which can be advantageously applied in applications for delivery of a medicament into the respiratory airways of beings, in which the medicament is made available e.g., either solved or dispersed, in the liquid that is to be sprayed. Based on the produced particle size, sprayed particles, either in a liquid state or in a solid state after quick drying, can be directed selectively to a desired specific region of the respiratory system.

From the prior art a spraying device is known for producing a spray of particles in a carrier gas at an ambient pressure, which comprises a storage volume for a liquid substance; a nozzle having an inlet and an outlet, the nozzle inlet being coupled to the storage volume in fluid communication; a counter electrode; a controllable electric supply coupled between the nozzle and the counter electrode for providing a controllable electric field between the nozzle outlet and the counter electrode.

The carrier gas can be either ambient, a supplied carrier gas or a specifically selected gas from a selected gas source.

However, it is observed in prior art such a spraying device the flow of particles may be quite limited. In an application where a dose of the medicament is to be administered, it is preferred that the time for administering is as short as possible. For this reason, relatively higher flows of spray are desirable.

Additionally, it is known that medicaments can be solved or dispersed in various carrying liquids such as ethanol or water.

It is observed that physical and/or chemical properties of the carrying liquid to be sprayed can affect the efficiency of the electrospraying process. In particular, water has a relatively high surface tension, which adversely affects the formation of a spray at the outlet of the nozzle. For water as carrying liquid, the electric field strength has to be so high that discharges are generated between nozzle and counter electrode that disturb the spray formation and interfere with a proper use for administering water based medicaments.

It is an object of the present invention to provide a spraying device and spraying method that overcome or mitigate one or more of the disadvantages of the prior art.

SUMMARY OF THE INVENTION

The object of the invention is achieved by a spraying device for producing a spray of particles in a carrier gas at an ambient pressure, comprising a storage volume for a liquid substance;
at least one nozzle having an inlet and an outlet, the nozzle inlet being coupled to the storage volume in fluid communication;
a counter electrode;
an electric supply coupled between the at least one nozzle and the counter electrode for providing a first potential between the nozzle outlet and the counter electrode so as to create a first electric field between the nozzle outlet and the counter electrode,
wherein the spraying device further comprises at least one discharge electrode, the at least one discharge electrode being coupled to the electric supply for providing a second potential between the discharge electrode and the counter electrode, the polarity of the second potential being opposite to the polarity of the first potential, and
wherein the at least one nozzle and the at least one discharge electrode are arranged adjacent and parallel to each other and facing the counter electrode from a substantially same direction.

Advantageously, the discharge electrode is capable of generating a corona discharge which creates an electric wind towards the counter electrode which is substantially parallel to the flow of sprayed particles from the nozzle towards the discharge electrode. The electric wind assists with the propagation of the droplets of spray by increasing the flow rate of the spray and thus shorten the time to administer a dosage to a being.

In an embodiment, the counter electrode is arranged to be at a potential intermediate the first and second potential.

Preferably, the intermediate potential at the counter electrode is set as ground level.

Moreover, the electric wind overcomes a further disadvantage from the prior art since in prior art system and method the sprayed particles are charged a deposition of the particles at a nearby surface such as the mouth or tracheal parts of the lung system of the being is very probable which would reduce the dosage of the medicament reaching the desired specific region of the respiratory system.

Advantageously, the oppositely charged ions in the electric wind will also discharge the particles in the spray making it for the particles possible to penetrate deeply into the respiratory tract without unwanted deposition.

According to an aspect, the present invention relates to a spraying device as described above, wherein the at least one discharge electrode is located in a proximity of the at least one nozzle separated by an intermediate air gap for preventing discharge between them.

According to an aspect, the present invention relates to a spraying device as described above, wherein a wall is arranged between the at least one nozzle and the discharge electrode.

According to an aspect, the present invention relates to a spraying device as described above, wherein the discharge electrode is a corona wire or corona tip.

According to an aspect, the present invention relates to a spraying device as described above, wherein the counter electrode is selected as one from a group comprising a perforated plate, a mesh, a ring and a rod-shaped electrode.

According to an aspect, the present invention relates to a spraying device as described above, wherein the electric supply is controllable for controlling a value of the first potential and/or a value of the second potential.

According to an aspect, the present invention relates to a spraying device as described above, wherein the electric supply is a high voltage generator capable of producing a pulsed high voltage as the first potential.

According to an aspect, the present invention relates to a spraying device as described above, wherein the electric supply is a high voltage generator capable of producing a pulsed high voltage as the second potential.

According to an aspect, the present invention relates to a spraying device as described above, wherein the electric supply is arranged for controlling at least one of a pulse shape, a pulse duration and a pulse frequency of the pulsed high voltage.

According to an aspect, the present invention relates to a spraying device as described above, wherein the pulse high voltage varies from a reduced high voltage level to a predetermined high voltage level, wherein the reduced high voltage level is in between ground level and the predetermined high voltage level.

According to an aspect, the present invention relates to a spraying device as described above, wherein the pulse frequency is up to about 10.000 Hz.

According to an aspect, the present invention relates to a spraying device as described above, wherein at least a portion at a tip of the outlet of the at least one nozzle has an outer surface comprising a coating of a coating material that has the property to be repulsive for the liquid substance to be sprayed.

According to an aspect, the present invention relates to a spraying device as described above, wherein at least a portion at a tip of the outlet of the at least one nozzle has an outer surface comprising an hydrophobic coating.

According to an aspect, the present invention relates to a spraying device as described above, wherein the spraying device has at least two nozzles adjacent and parallel to each other and each nozzle is arranged with at least one dedicated discharge electrode.

According to an aspect, the present invention relates to a spraying device as described above, wherein the counter electrode is a single common electrode for each nozzle and its dedicated discharge electrode.

According to an aspect, the present invention relates to a spraying device as described above, wherein the at least one nozzle is arranged in a substantially cylindrical housing; an end surface of the housing being opening at the side of the nozzle outlet for outflow of the produced spray; the housing having a further opening at an opposite end surface or in the cylinder wall near an opposite end surface for an inflow of the carrier gas.

According to an aspect, the present invention relates to a spraying device as described above, wherein the storage volume is a collapsible bag or pouch adapted to provide the liquid substance to the nozzle inlet at ambient pressure level.

According to an aspect, the present invention relates to a spraying device as described above, wherein the at least one nozzle is a capillary needle which is dimensioned with an internal diameter and a length in such a way that the capillary needle locks the storage volume by means of a capillary force, if no electric field between the at least one nozzle and the counter electrode is present.

According to an aspect, the present invention relates to a spraying device as described above, wherein at least one or each of the first and second electric supplies may comprise adjustment means for adjusting the potential settings of the respective electric supply so as to create a neutrally or weakly charged spray by balancing a current from the corona discharge with a current from the nozzle for balancing the charge of ions from the corona discharge with the charge of the spray particles.

According to an aspect, the present invention relates to a spraying device as described above, wherein the liquid substance to be sprayed is based on a solvent selected from water and organic liquids such as alcohols.

According to an aspect, the present invention relates to a spraying device as described above, wherein the liquid substance to be sprayed is selected from an emulsion and a suspension.

Further the present invention relates to a method for producing from a liquid substance a spray of particles in a carrier gas at an ambient pressure, comprising providing at least one nozzle having an inlet and an outlet, the nozzle inlet being coupled to a storage volume in fluid communication, the storage volume adapted for containing the liquid substance;

providing a counter electrode;

providing at least one discharge electrode, wherein the at least one nozzle and the at least one discharge electrode are arranged adjacent and parallel to each other and facing the counter electrode from a substantially same direction, providing a first potential between the nozzle outlet and the counter electrode so as to create a first electric field between the nozzle outlet and the counter electrode and produce the spray of particles from the liquid substance parallel to the first electric field, and providing a second potential between the discharge electrode and the counter electrode, the polarity of the second potential being opposite to the polarity of the first potential so as to create a second electric field between the discharge electrode and the counter electrode and produce a corona discharge at the discharge electrode for providing an electric wind in a substantially same direction as the spray of particles.

According to an aspect, the present invention relates to a method as described above, wherein the second potential is set to a value for producing an intensity of the corona discharge adapted for substantially neutralizing charged particles in the spray of particles.

According to an aspect, the present invention relates to a method as described above, wherein at least one of the first potential and the second potential is produced as a pulsed high voltage.

Advantageous embodiments are further defined by the dependent claims.

BRIEF DESCRIPTION OF THE DRAWINGS

The invention will be explained in more detail below with reference to a few drawings in which illustrative embodiments thereof are shown. They are intended exclusively for illustrative purposes and not to restrict the inventive concept, which is defined by the claims.

FIG. 1 shows a cross-sectional view of a spraying device according to an embodiment of the invention;

FIG. 2 shows the cross-section of FIG. 1 in which a region of a flow of a spray and regions of electric wind are shown;

FIG. 3 shows a perspective view of the spraying device of FIG. 1;

FIG. 4 shows a perspective view of a spraying device according to an embodiment of the invention;

DETAILED DESCRIPTION

Figure 1:
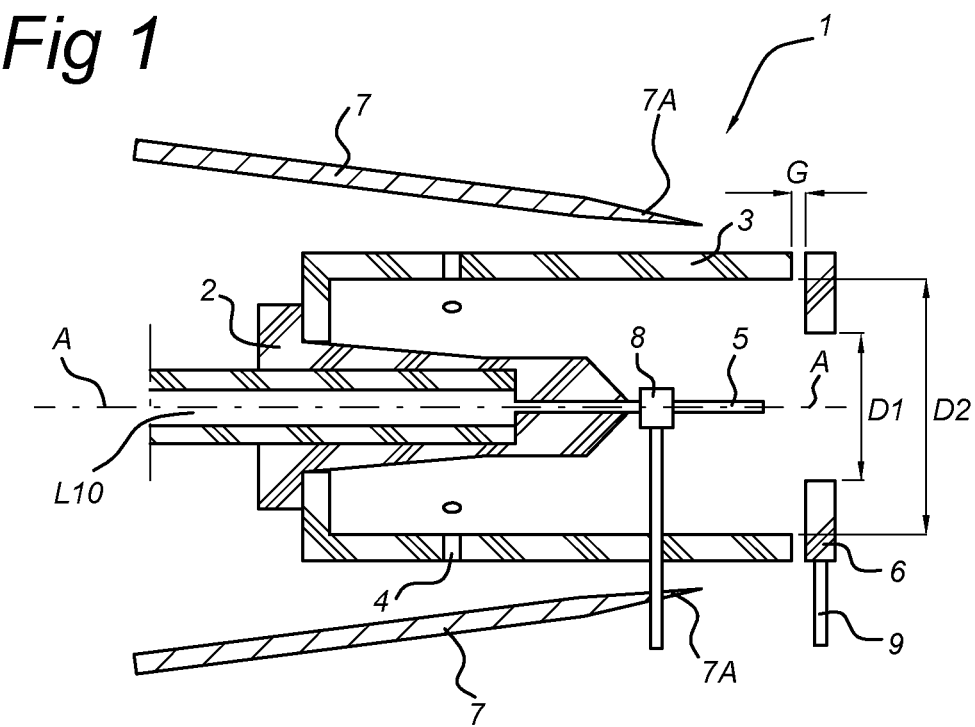

In the following figures, the same reference numerals refer to similar or identical components in each of the figures.

FIG. 1 shows a cross-sectional view of a spraying device according to an embodiment of the invention.

In the embodiment, the spraying device 1 comprises a nozzle with an inlet assembly 2 and an outlet 5, i.e. a hollow needle. The inlet assembly 2 is coupled to a storage volume (not shown) through a connection, e.g., a tube 10.

Further the inlet assembly 2 comprises an insulating wall element 3, preferably a cylindrical wall element 3, that surrounds and is parallel to the nozzle outlet 5. In an embodiment, the main body axis of the cylindrical wall element is arranged to coincide with the longitudinal axis of the nozzle.

The cylindrical wall element 3 has an open end surface proximate to the location of the nozzle outlet 5. Also, the cylindrical wall element 3 may comprise one or more openings 4 in the cylindrical wall and/or an open end surface proximate to the location of the nozzle inlet for inflow of carrier gas.

It is noted that in some embodiments the cylindrical wall element 3 may be optional.

At the open end surface 3a the spraying device 1 comprises a counter electrode 6, which is arranged at a small distance G from the open end surface 3a.

The counter electrode 6 has an opening or perforation for allowing during use that a spray ejected from the nozzle outlet can pass through the counter electrode. The opening or perforation may have any suitable shape.

The counter electrode 6 may be a plate that has an opening wherein the plate is arranged at some distance from the cylindrical wall element 3.

The end of the nozzle outlet may be located on the same side of the plate as the wall element, but optionally, the nozzle outlet may extend through the plate.

In an embodiment, the size D1 of the opening may be smaller than the inner diameter D2 of the cylindrical element. However, as will be appreciated by the skilled in the art, embodiments are conceivable where the size D1 is either substantially equal or larger than diameter D2.

In a further embodiment, the counter electrode 6 is substantially ring-shaped.

In an alternative embodiment, the counter electrode 6 may comprise a mesh or one or more rod-shaped electrodes.

Further, the spraying device 1 comprises at least one further electrode 7 which in use acts as discharge electrode. The discharge electrode 7 is arranged in proximity to the nozzle, and in this embodiment outside of the cylindrical wall 3.

The discharge electrode 7 is separated from the nozzle (or the cylindrical wall element) by an air gap to avoid discharge between the nozzle and discharge electrode. The discharge electrode is directed substantially parallel to the longitudinal axis A of the nozzle and positioned at a same side of the counter electrode 6.

In an embodiment, per nozzle outlet 5 a plurality of discharge electrodes 7 is arranged around the longitudinal axis of the nozzle to obtain an electric field around the nozzle when a voltage is applied between the nozzle and the discharge electrodes.

In a further embodiment, the plurality of discharge electrodes 7 is symmetrically arranged around the longitudinal axis of the nozzle to obtain a symmetrical electric field around the nozzle.

Further, the spraying device comprises an electric supply (not shown) that is coupled between a contact 8 of the nozzle 5 and a contact 9 of the counter electrode 6 for providing a first potential V1 to the nozzle outlet and ground potential to the counter electrode so as to create a first electric field between the nozzle outlet and ground. Basically this first electric field drives the electrospraying process by charging the liquid at the nozzle outlet which results in the atomization of the liquid to charged particles. Further the first electric field causes that charged particles move from the nozzle towards the plane of the counter electrode so as to create the flow of particles, i.e. the spray.

A second potential V2 with a polarity opposite to the polarity of the first potential is provided between the discharge electrode(s) and the counter electrode. In this manner, the counter electrode is set at an intermediate (ground) potential between the nozzle outlet and the discharge electrode(s), and the counter electrode will act as a common electrode for the nozzle outlet and the discharge electrode(s).

To this end, the spraying device is arranged with an electric supply (not shown) in such a way that in use a second electric field is created between the discharge electrode(s) 7 and the counter electrode 6 which causes that when the second electric field between the discharge electrode(s) 7 and the counter electrode 6 is high enough, a corona discharge will occur at a tip 7a of the discharge electrode(s) 7 and per consequence ions produced in the corona discharge will accelerate towards the counter electrode and an electric wind will become active.

Each discharge electrode 7 is arranged with a tip shaped end 7a, which intensifies the local electric field and thus enhances the creation of the corona discharge.

In an embodiment, the nozzle is a capillary needle.

Figure 2:
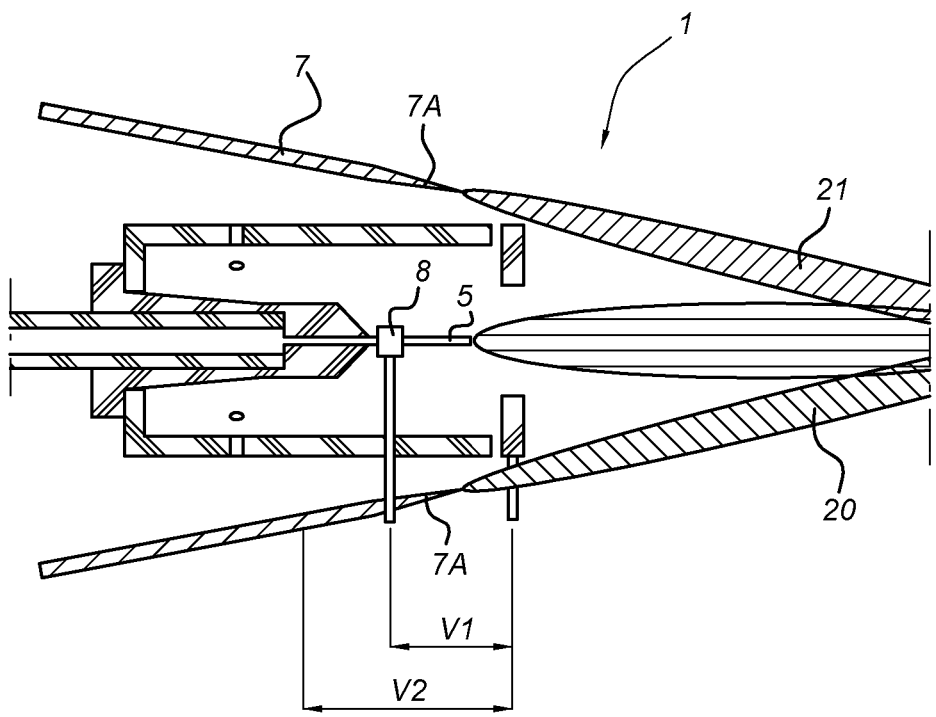
Figure 3:
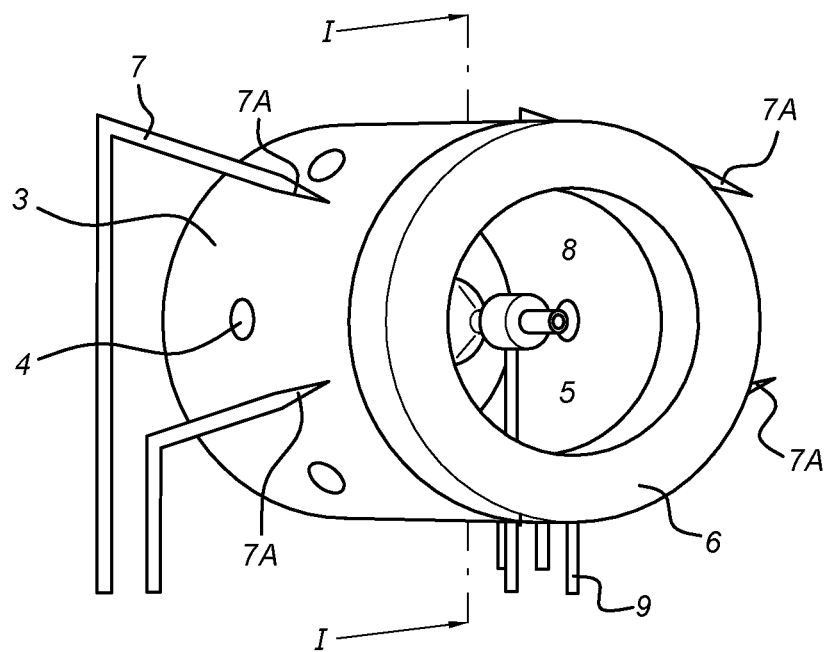
Figure 4:
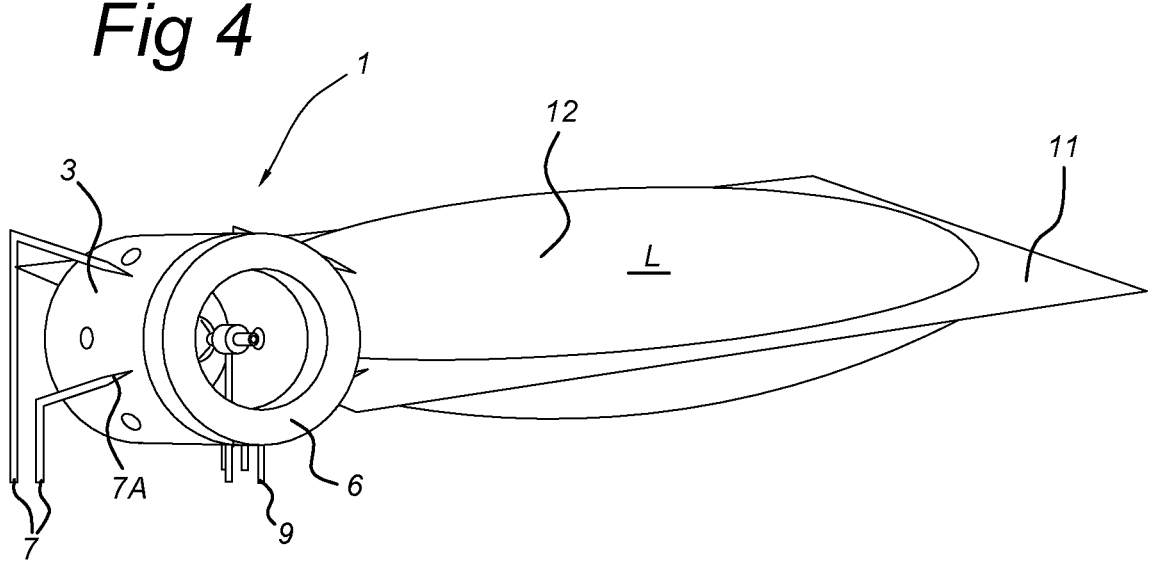
Figure 5:
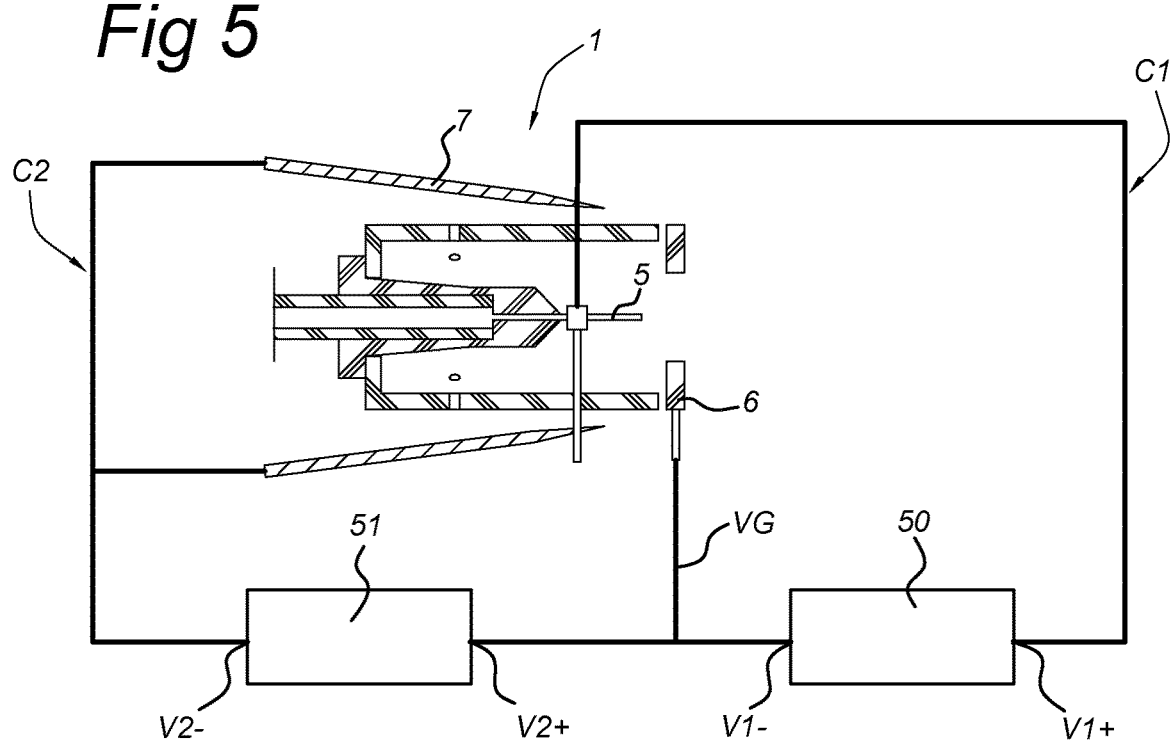
FIG. 5 shows a schematic layout of the electric circuit of the spraying device according to an embodiment of the invention.

FIG. 2 shows a detail of the cross-section of FIG. 1. In FIG. 2 a use of the spraying device is illustrated.

A liquid L to be sprayed is entering the hollow needle of the nozzle outlet 5 through tube 10. The liquid to be sprayed i.e. a solution of solute and solvent may be based on a solvent selected from water and organic liquids such as alcohols. Additionally, the liquid to be sprayed may be an emulsion or suspension.

At the tip of the nozzle outlet 5 the liquid L is submitted to a first electrical force obtained by applying the high voltage V1 of first polarity (e.g. a positive voltage) between the nozzle outlet by way of its connecting electrode 8 and the counter electrode 6 which may be embodied as a flat metal ring. If the high voltage potential is high enough, the tip of the nozzle outlet will produce a spray of very fine droplets, shown by area 20 in the figure, which propagates in a spraying direction which is mainly determined by the first electric field.

The discharge electrodes 7 are connected to a high voltage source of a second polarity, of opposite sign with respect to the first polarity (e.g. a negative voltage) while the counter electrode 6 is used as ground to create a second electrical field by second potential V2. When the second electric field between the discharge electrodes 7 and the counter electrode 6 is high enough, a corona discharge will occur and per consequence an electric wind 21 will become active. The electric wind 21 passes the plane of the counter electrode and is directed to intersect with the spray 20. The electric wind is directed under a relatively small angle with the spray direction and has a relatively large velocity component in predominantly the same direction.

The skilled in the art will appreciate that the geometry of the counter electrode and the position of the discharge electrode with respect to the nozzle outlet and the counter electrode can be arranged in such a way that the electric wind 21 may pass the counter electrode and intersect with the spray 20.

By intersecting with the spray, the electric wind 21 helps to propagate the droplets of spray 20 by adding impulse to spray 20 in the spray direction, but additionally the oppositely charged ions in the electric wind 21 will assist the discharge of the droplets in the spray 20. It is noted that by controlling the intensity of the corona discharge relative to the formation of the charged spray, the spray can have a substantially neutral charge. As a result, the neutral particles can penetrate deeply into the respiratory tract of the being administered with the spray without unwanted deposition, which advantageously improves the administering process of a medicament being present in the particles of liquid L.

FIG. 3 shows a perspective view of the spraying device of FIG. 1. In the embodiment shown here, the nozzle outlet 5 is symmetrically surrounded by four discharge electrodes 7 that are directed substantially parallel to the longitudinal axis of the nozzle.

FIG. 4 shows a perspective view of a spraying device according to an embodiment of the invention.

Concerning the liquid to be sprayed, this is in general quite complex because a constant pressure is needed. This makes that often complex and costly solutions like syringe pumps are needed to do this job.

In an embodiment, the spraying device is arranged with a collapsible or deformable container which allows for a flow controlled solution. A highly flexible container 11, consisting of a pouch or bag with flexible walls 12, is filled with the liquid L to be aerosolized by the electro-spray. In this embodiment atmospheric pressure on the outside of the flexible container 11 is used for displacing the liquid L towards the tube 10 and the nozzle 5 while the flexible container collapses (or deforms) under the pressure. The flow of liquid (i.e. and thus the spraying dosage) can be controlled by selecting the internal diameter of the nozzle in such a way that a capillary force will act on the liquid to fill the volume of the nozzle with the liquid from the container. The formation of spray from the liquid in the nozzle is driven by the electrical force of the first potential.

The length and/or the diameter of the nozzle can tuned to obtain such a high capillary force that a capillary lock for the liquid is created.

Optionally in some embodiments, where dimensions of the nozzle prevent the creation of a capillary lock, a mechanical lock may be provided on the nozzle.

Another dosage control is the dilution ratio of the active material and the carrier liquid in the flexible container (11).

FIG. 5 shows a schematic layout of the electric circuit of the spraying device according to an embodiment of the invention.

In this embodiment, in a first circuit C1 a first electric supply 50 is coupled between the nozzle outlet 5 and the counter electrode 6 for creating a high voltage between the electrodes 5, 6.

In this embodiment a positive terminal V1+ of the first electric supply 50 is connected to the nozzle so as to have a positive potential on the nozzle while a negative terminal V1− is connected to the counter electrode 6.

In a second circuit C2, a second electric supply 51 is coupled between the discharge electrode(s) 7 and the counter electrode 6 for creating a high voltage between the electrodes 6, 7.

A negative terminal V2− of the second electric supply 51 is connected to the discharge electrode 7 so as to have a negative potential on the discharge electrode while a positive terminal V2+ is connected to the counter electrode 6, simultaneously with the negative terminal of the first electric supply.

The potential on the counter electrode is selected as ground level VG.

The skilled in the art will appreciate that switching means will be arranged within each of the first and second electric circuits to allow control of the respective electric supply.

Further, at least one or each of the first and second electric supplies may comprise adjustment means for adjusting the potential settings of the respective electric supply. In this manner, the current from the corona discharge can be balanced with the current from the nozzle to allow to balance the charge of ions from the corona discharge with the charge of the spray particles so as to create a neutrally or weakly charged spray.

In a further embodiment, the first electric supply 50 and the second electric supply 51 are each arranged as high voltage pulse generators.

Such a type of high voltage pulse electric supply is controlled by for example a pulse shaping or timing circuit that makes that the high voltage potential is produced only during a set time. In this manner, the production of the spray and/or the electric wind takes place only during a time set by the pulse shaping or timing circuit.

Advantageously, by pulsing the elective potential between the nozzle and the counter electrode (for producing the spray) the prior art problem to spray water based substances can be overcome. In the prior art when spraying water based substances the relatively high surface tension of water adversely affects the spraying process because for water based substances the electric voltage to create a continuous cone jet (to generate a spray) is well above the discharge voltage.

By applying a pulsed high voltage potential, the effect of the electric discharge between the nozzle outlet and the counter electrode is prevented. During prior art spraying of water just below the sparking voltage the space charge causes the conical meniscus to relax back to a spherical one, which affects the spraying process and the size of the created particles. The relaxation process typically results in a spontaneous pulsation of the spray with varying and uncontrollable particle size.

When according to the invention using a pulsed high voltage potential, the electric field is kept below the sparking voltage (discharge voltage). The pulsation is regulated in such a way that the spraying is interrupted to remove space charge. As a result the spraying process and particle size are controllable.

Alternatively or additionally, a liquid with a lower surface tension than water may be added to the water based substance to enhance the spraying properties of the substance.

It is noted that this mechanism may also be active in other liquids with relative high surface tension, where this disadvantage can be overcome by the present invention.

Further it is noted that in an embodiment either only the first electric supply or only the second electric supply or both first and second electric supplies may be arranged as a pulsed high voltage supply.

Figure 6:
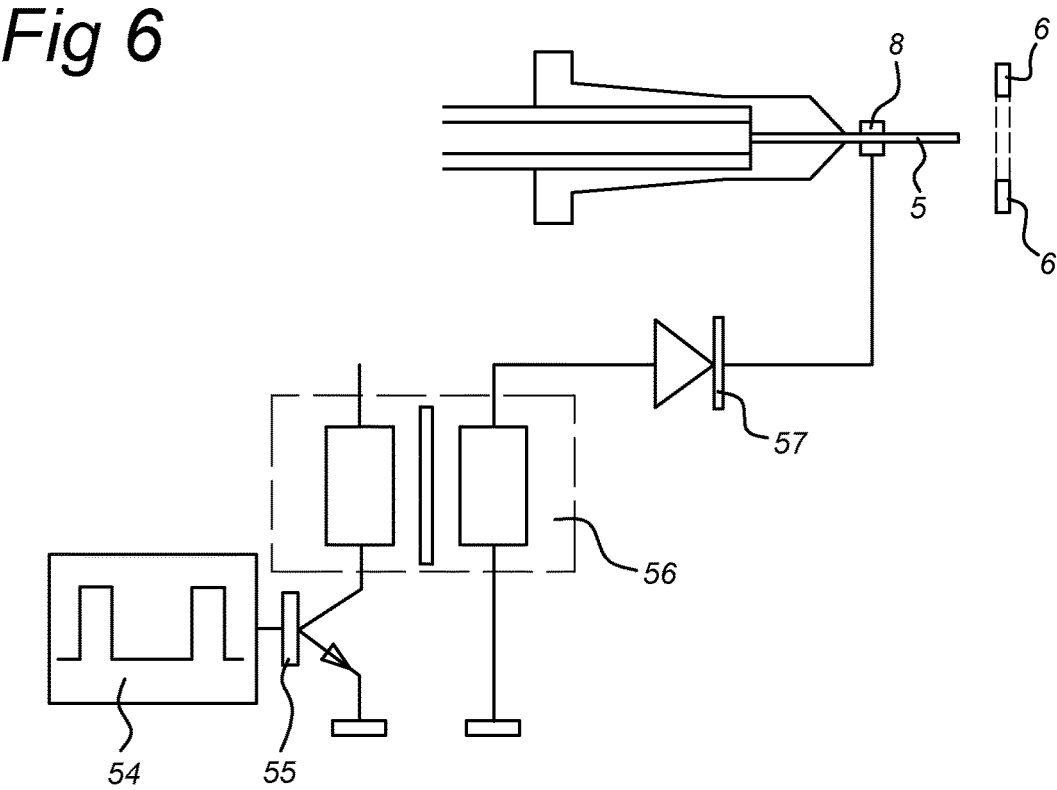
FIG. 6 shows a schematic layout of the electric circuit of the spraying device according to an embodiment of the invention.

FIG. 6 shows a schematic layout of the electric supply circuit of the spraying device according to an embodiment of the invention.

In FIG. 6, the electric supply circuit comprises a pulse generator 54, a transistor 55, a high voltage transformer 56 and a diode 57.

The pulse generator 54 is coupled with an output to a switching transistor, which is arranged for switching the primary side of the high voltage transformer 56. The secondary side of the transformer 56 is connected to an anode of the diode 57. The cathode of the diode 57 is connected to the contact 8 of the nozzle outlet 5. In use, the electric circuit causes a voltage pulse generated by the pulse generator 54 to be supplied as a high voltage pulse to the nozzle outlet.

The pulse generator 54 may be a variable pulse generator with the capability to select at least one of a pulse with a desired shape, and/or a desired pulse length and interval, and/or a pulse frequency.

For spraying water based substances in carrier, a pulse frequency up to about 10.000 Hz may be used for effective suppression of the discharge between the nozzle outlet and the counter electrode.

In an embodiment, the pulse voltage varies from ground level to a predetermined high voltage level.

For example, the pulse voltage varies between 0 and about 5 kV.

In an embodiment, the pulse voltage varies from a reduced high voltage level to a predetermined high voltage level, wherein the reduced high voltage level is in between ground level and the predetermined high voltage level. For example, the predetermined high voltage level is about 5 kV.

The pulses as produced can have any shape as known in the art, for example, can have a shape selected from a rectangular, triangular, sawtooth or sinusoid shape.

Figure 7:
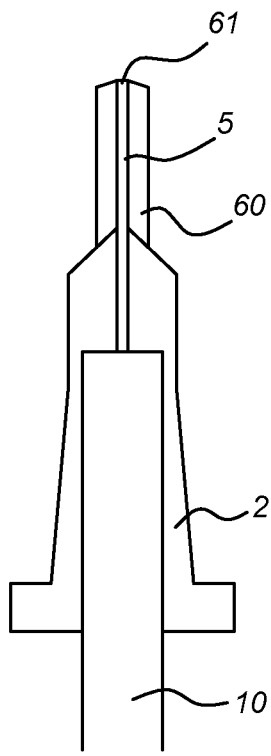
FIG. 7 shows a cross-sectional view of a nozzle of the spraying device according to an embodiment of the invention.

FIG. 7 shows a cross-sectional view of a nozzle of the spraying device according to an embodiment of the invention.

For some substances, a wetting of the outer surface of the nozzle outlet may occur. It is desired that the area of the nozzle tip that acts as a base for creation of the spraying cone is well defined.

To achieve this object, in an embodiment, the nozzle outlet 5 which is embodied as a metal needle, for example a steel needle, comprises a coating 60 on the outer surface of the needle. The coating 60 comprises a coating material that has the property to be repulsive for the liquid to be sprayed.

In an embodiment where the liquid is water or water based, the coating 60 comprises a coating material that has hydrophobic properties.

Alternatively, the material of the nozzle is selected to have the property to be repulsive for the liquid to be sprayed, or in case of a water based solution to be hydrophobic.

The coating material is arranged as a layer that covers the outer diameter of the nozzle at least at the tip of the nozzle, preferably over the full length of the nozzle outlet.

In this manner, the nozzle outlet with the hydrophobic coating 60 has the capability to prevent wetting of the outer surface of the nozzle by water which advantageously results in a formation of a relatively smaller liquid cone with substantially the same diameter as the nozzle opening 61.

In an embodiment, the end of the layer of coating material is at level with the tip of the nozzle outlet, in such a way that the opening in the coating material is substantially equal to the opening 61 of the nozzle outlet.

Alternatively, the end of the layer of coating material is positioned slightly below level with the tip of the nozzle outlet, to leave a short length of the tip of the nozzle exposed.

As will be appreciated by the skilled in the art, the arrangement and/or position of the coating layer at the tip of nozzle outlet and the extent of exposure of the outer surface of the tip may depend on desired spraying properties, on properties of the substance to be sprayed, etc.

In an embodiment, the end of the layer of coating material is beveled at the tip of the nozzle.

It is noted that to avoid wetting of the nozzle outlet, the nozzle outlet may be covered either over its full length by the layer of coating material or over a portion of its length starting from the tip by a flange of coating material.

Figure 8:
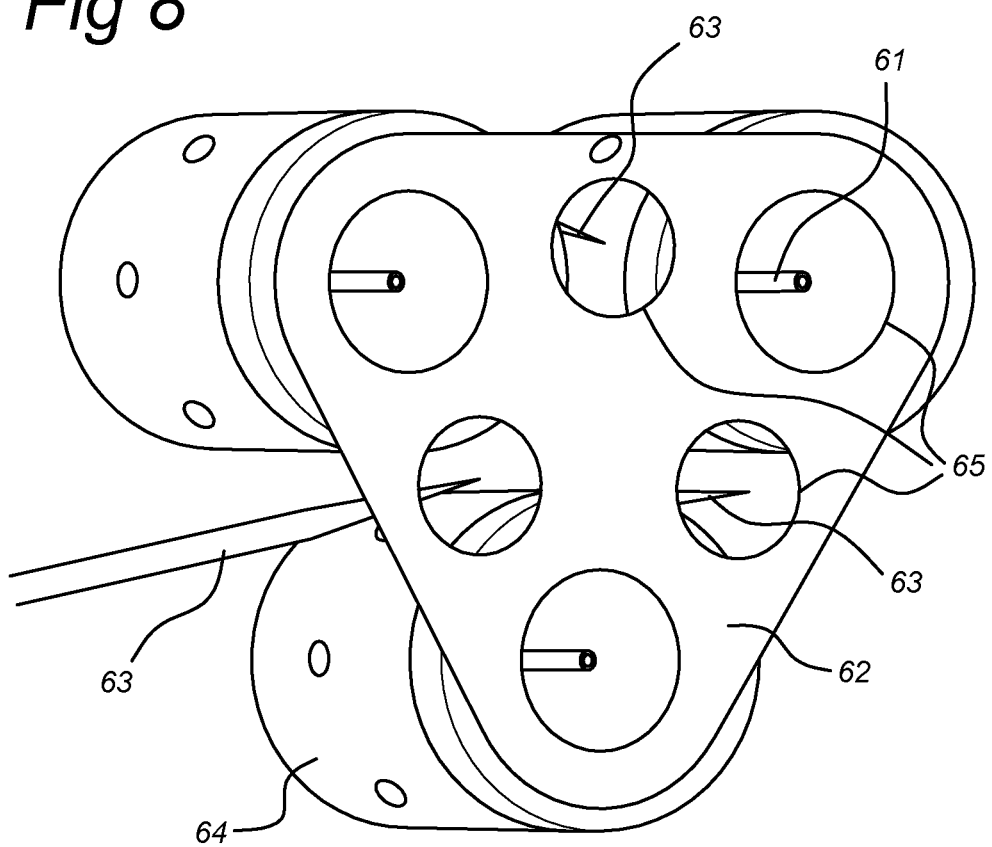
FIG. 8 shows a spraying device according to an embodiment of the invention.

FIG. 8 shows a spraying device according to an exemplary embodiment of the invention.

In the embodiment of FIG. 8, the spraying device is arranged with multiple nozzle outlets 61 and multiple discharge electrodes 63 and a single common counter electrode 62.

For example, in the spraying device three nozzle outlets 61 are arranged parallel to each other in a triangular set up. Each nozzle outlet 61 is surrounded by an insulating cylindrical wall element 64 that is parallel to the respective nozzle outlet. In between the cylindrical wall elements of each pair of nozzle outlets 61 a discharge electrode 63 is positioned.

The single common counter electrode 62 is placed in front of the nozzle outlets and the intermediate counter electrodes, separated from the respective tips of the nozzle outlets and discharge electrodes by an air gap. The counter electrode may consist of a substantially triangular plate with openings 65 facing the tips of the nozzle outlets 61 and the intermediate counter electrodes 63 at their respective positions.

In a further embodiment, the single common counter electrode is embodied as a mesh, or as a multitude of rings, wherein each ring is associated with one nozzle outlet.

It is noted that the spraying device can be advantageously applied in portable applications, a portable device, for delivery of medical components into the respiratory airways of beings. Due to the absence of a pumping system the particle delivery system can be dimensioned with relative ease for incorporation into an inhaler device. Also, since no pumping system is required, the power supply can be relatively small and portable, being battery-powered, since it needs to deliver only power for the generation of the spray which is as mentioned above in the order of micro- to milli-watts. Also, desktop applications of the spraying device are conceivable within the scope of the present invention. The discharge electrode(s) provide an enhanced flow of sprayed particles due to the creation electric wind from the corona discharge. Moreover the discharge electrodes provide a neutralization of the sprayed particles which allows an enhanced transport of the particles within the respiratory system.

The invention has been described with reference to some embodiments. Obvious modifications and alterations will occur to others upon reading and understanding the preceding detailed description. It is intended that the invention be construed as including all such modifications and alterations insofar as they come within the scope of the appended claims.

The invention claimed is:

1. A spraying device for producing a spray of particles in a carrier gas at an ambient pressure, comprising:
   a storage volume for a liquid substance;
   at least one nozzle having an inlet and an outlet, the nozzle inlet being coupled to the storage volume in fluid communication;
   a counter electrode having a circular opening a distance in front of the at least one nozzle;
   an electric supply coupled between the at least one nozzle and the counter electrode for providing a first potential between the nozzle outlet and the counter electrode so as to create a first electric field between the nozzle outlet and the counter electrode;
   multiple discharge electrodes being coupled to the electric supply for providing a second potential between the discharge electrodes and the counter electrode, the polarity of the second potential being opposite to the polarity of the first potential; and
   a wall arranged laterally adjacent to the discharge electrodes and the at least one nozzle, in which the wall is positioned laterally in between the at least one nozzle and each of the discharge electrodes, wherein the discharge electrodes surround the wall and are angled toward a tip of the at least one nozzle,
   wherein the at least one nozzle and the discharge electrodes are arranged in a like direction such that the nozzle and the discharge electrodes face the counter electrode.

2. The spraying device according to claim 1, wherein the discharge electrodes are located in a proximity of the at least one nozzle with an intermediate air gap for preventing discharge between them.

3. The spraying device according to claim 1, wherein the discharge electrodes is a corona wire or corona tip.

4. The spraying device according to claim 1, wherein the counter electrode is selected from a group comprising a perforated plate, a mesh, a ring and a rod-shaped electrode.

5. The spraying device according to claim 1, wherein the electric supply is controllable for controlling a value of the first potential and/or the second potential.

6. The spraying device according to claim 1, wherein the electric supply is a high voltage generator capable of producing a pulsed high voltage as the first potential.

7. The spraying device according to claim 6, wherein the electric supply is arranged for controlling at least one of a pulse shape, a pulse duration and a pulse frequency of the pulsed high voltage.

8. The spraying device according to claim 7, wherein the pulsed high voltage varies from a reduced high voltage level to a predetermined high voltage level, wherein the reduced high voltage level is in between ground level and the predetermined high voltage level.

9. The spraying device according to claim 7, wherein the electric supply is arranged for controlling the pulse frequency of the pulsed high voltage and wherein the pulse frequency is up to about 10.000 Hz.

10. The spraying device according to claim 1, wherein the electric supply is a high voltage generator capable of producing a pulsed high voltage as the second potential.

11. The spraying device according to claim 1, wherein at least a portion at a tip of the outlet of the at least one nozzle has an outer surface comprising a coating of a coating material that has the property to be repulsive for the liquid substance to be sprayed.

12. The spraying device according to claim 1, wherein at least a portion at a tip of the outlet of the at least one nozzle has an outer surface comprising a hydrophobic coating.

13. The spraying device according to claim 1, wherein the spraying device has at least two nozzles adjacent and parallel to each other and each nozzle is arranged with at least one dedicated discharge electrode.

14. The spraying device according to claim 13, wherein the counter electrode is a single common electrode for each nozzle and its dedicated discharge electrode.

15. The spraying device according to claim 1, wherein the at least one nozzle is arranged in a substantially cylindrical housing;
   an end surface of the housing being open at the side of the nozzle outlet for outflow of the produced spray;
   the housing having a further opening at an opposite end surface or in a cylinder wall near an opposite end surface for an inflow of the gas.

16. The spraying device according to claim 1, wherein the storage volume is a collapsible bag or pouch adapted to provide the liquid substance to the nozzle inlet at ambient pressure level.

17. The spraying device according to claim 1, wherein the at least one nozzle is a capillary needle which is dimensioned with an internal diameter and a length in such a way that the capillary needle locks the storage volume by means of a capillary force, if no electric field between the at least one nozzle and the counter electrode is present.

18. The spraying device according to claim 1, wherein the liquid substance to be sprayed is based on a sol vent selected from water and organic liquids, including alcohols.

19. The spraying device according to claim 1, wherein the liquid substance to be sprayed is selected from an emulsion and a suspension.

20. The spraying device according to claim 1, wherein the discharge electrodes are symmetrically arranged around the longitudinal axis of the at least one nozzle.

21. A method for producing from a liquid substance a spray of particles in a carrier gas at an ambient pressure, comprising:
   providing at least one nozzle having an inlet and an outlet, the nozzle inlet being coupled to a storage volume in fluid communication, the storage volume containing the liquid substance;
   providing a counter electrode having a circular opening a distance in front of the at least one nozzle;
   providing multiple discharge electrodes, wherein the at least one nozzle and the discharge electrodes are arranged adjacent and parallel to each other and facing the counter electrode from a substantially same direction;
   providing a first potential between the nozzle outlet and the counter electrode so as to create a first electric field between the nozzle outlet and the counter electrode and produce the spray of particles from the liquid substance parallel to the first electric field;
   providing a wall laterally adjacent to the discharge electrodes and the at least one nozzle, in which the wall is positioned laterally in between the at least one nozzle and each of the discharge electrodes, wherein the discharge electrodes surround the wall and are angled toward a tip of the at least one nozzle,; and
   providing a second potential between the discharge electrodes and the counter electrode, the polarity of the second potential being opposite to the polarity of the first potential so as to create a second electric field between the discharge electrodes and the counter electrode and produce a corona discharge at the discharge electrodes for providing an electric wind in the substantially same direction as the spray of particles.

22. The method according to claim 21, wherein the second potential is set to a value for producing an intensity of the corona discharge adapted for either substantially neutralizing charged particles in the spray of particles or creating a weakly charged spray of particles.

23. The method according to claim 21, wherein at least one of the first potential and the second potential is produced as a pulsed high voltage.

* * * * *